US00PP15640P2

(12) United States Plant Patent
Heuger

(10) Patent No.: US PP15,640 P2
(45) Date of Patent: Mar. 8, 2005

(54) *HELLEBORUS* PLANT NAMED 'HGC JERICHO'

(50) Latin Name: *Helleborus niger*
Varietal Denomination: HGC Jericho

(76) Inventor: Joseph Heuger, Münsterstrasse 49, 49129 Glandorf (DE)

( * ) Notice: Subject to any disclaimer, the term of this patent is extended or adjusted under 35 U.S.C. 154(b) by 0 days.

(21) Appl. No.: 10/878,420

(22) Filed: Jun. 28, 2004

(51) Int. Cl.[7] ..... A01H 5/00
(52) U.S. Cl. ..... Plt./263
(58) Field of Search ..... Plt./263

(56) References Cited

PUBLICATIONS

Sunset National Garden Book Mar. 1997, Sunset Books, Menlo Park CA, p. 331.*

UPOV ROM GTITM Computer Datbase, GTI Jouve Retrieval Software 2004/40 Citation(s) for 'HGC Jericho'.*

Huxley, Anthony, ed. RHS Dictionary of Gardening, vol. 2 D–K. New York: The Stockton Press: 1992. pp. 538–542.*

Wayside Gardens Autumn Catalog 1999; cover, last page and p. 72.*

Seyring, M. In vitro cloning of *Helleborus niger*. Plant Cell Reports 20 (10): p 895–900 Mar. 2002 (abstract).*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Helleborus* plant named 'HGC Jericho', characterized by its compact plant habit; dark green-colored leaves; large white-colored flowers; and relatively early flowering.

1 Drawing Sheet

Botanical classification/cultivar designation: *Helleborus niger* cultivar HGC Jericho.

BACKGROUND OF THE INVENTION

The present Invention relates to a new and distinct cultivar of *Helleborus* plant, botanically known as *Helleborus niger,* and hereinafter referred to by the cultivar name HGC Jericho.

The new *Helleborus* is a product of a planned breeding program conducted by the Inventor in Glandorf, Germany. The objective of the breeding program was to create new *Helleborus* cultivars with a good plant habit, that flower for a long period of time, and have attractive flower coloration.

The new *Helleborus* originated from a cross-pollination made by the Inventor in November, 1997 in Glandorf, Germany of an unnamed seedling of *Helleborus niger,* not patented, as the female, or seed, parent with an unnamed seedling of *Helleborus niger,* not patented, as the male, or pollen, parent. The new *Helleborus* was discovered and selected by the Inventor as a flowering plant within the progeny of the stated cross-pollination in a controlled environment in Glandorf, Germany.

Asexual reproduction of the new cultivar by divisions at Glandorf, Germany since March, 2000, has shown that the unique features of this new *Helleborus* are stable and reproduced true to type in successive generations.

SUMMARY OF THE INVENTION

Plants of the cultivar HGC Jericho have not been observed under all possible environmental conditions. The phenotype may vary somewhat with variations in environment such as temperature and light level without, however, any variance in genotype.

The following traits have been repeatedly observed and are determined to be the unique characteristics of 'HGC Jericho'. These characteristics in combination distinguish 'HGC Jericho' as a new and distinct cultivar of *Helleborus:*

1. Compact plant habit.
2. Dark green-colored leaves.
3. Large white-colored flowers.
4. Relatively early flowering.

Plants of the new *Helleborus* have darker green-colored leaves and flower about one month earlier than plants of the female parent. Compared to plants of the male parent, plants of the new *Helleborus* have larger flowers and flower about one month later.

Plants of the new *Helleborus* can be compared to the *Helleborus orientalis* Hybrid cultivar HGC Double Surprise, disclosed in U.S. Plant patent application Ser. No. 10/878,418. In side-by-side comparisons conducted in Glandorf, Germany, plants of the new *Helleborus* differed from plants of the cultivar HGC Double Surprise in the following characteristics:

1. Plants of the new *Helleborus* were shorter than plants of the cultivar HGC Double Surprise.
2. Plants of the new *Helleborus* had shorter leaf petioles than plants of the cultivar HGC Double Surprise.
3. Plants of the new *Helleborus* had single flowers whereas plants of the cultivar HGC Double Surprise had double flowers.
4. Plants of the new *Helleborus* had larger flowers than plants of the cultivar HGC Double Surprise.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Helleborus*.

The photograph at the top of the sheet comprises a side perspective view of a typical flowering plant of 'HGC Jericho'.

The photograph at the bottom of the sheet is a close-up view of a typical flowering of 'HGC Jericho'.

DETAILED BOTANICAL DESCRIPTION

The aforementioned photographs, following observations and measurements describe plants grown in Glandorf, Germany, in a glass-covered greenhouse and under commercial production practices during the winter. Plants were grown in 15-cm containers and were about six months old when the photographs and description were taken. During the production of the plants, day temperatures were about 18° C. and night temperatures were about 14° C. In the following description, color references are made to The Royal Horticultural Society Colour Chart, 1995 Edition, except where general terms of ordinary dictionary significance are used.

Botanical classification: *Helleborus niger* cultivar HGC Jericho.

Parentage:

*Female parent.*—Unnamed seedling of *Helleborus niger,* not patented.

*Male parent.*—Unnamed seedling of *Helleborus niger,* not patented.

Propagation:

*Type.*—By divisions.

*Time to initiate roots, winter.*—About 40 days at 12° C.

*Time to produce a rooted plant, winter.*—About six months at 12 to 15° C.

*Root description.*—About 3 to 15 thick fleshy roots; not branching; white to brown in color.

Plant description:

*Plant form/habit.*—Compact plant habit; moderately vigorous growth habit. Leaves basal. Single flower form.

*Plant height.*—About 16 cm.

*Plant width* (*spread*).—About 27 cm.

*Foliage description.*—Arrangement: Basal; palmately compound with four to nine leaflets per leaf. Leaflet length: About 5 to 8.5 cm. Leaflet width: About 1.5 to 4 cm. Leaflet shape: Lanceolate; pedate. Leaflet apex: Broadly acuminate. Leaflet base: Acute. Leaflet margin: Serrate. Texture, upper and lower surfaces: Smooth, glabrous. Venation pattern: Reticulate. Color: Developing leaflets, upper surface: 137A. Developing leaflets, lower surface: Closest to 137C. Fully expanded leaflets, upper surface: 147A. Fully expanded leaflets, lower surface: Closest to 147B. Venation, upper and lower surfaces: 146C. Petiole: Length: About 4 cm. Diameter: About 4 mm. Texture, upper and lower surfaces: Smooth, glabrous. Color, upper and lower surfaces: 146C overlain with 175A.

Flower description:

*Flower type/habit.*—Single rounded flowers arranged singly on short peduncles; flowers face upright to outwardly; petals inconspicuous. Freely flowering habit with about 15 flowers developing per plant over the flowering period.

*Fragrance.*—Slightly fragrant.

*Natural flowering season.*—Early flowering; intermittent flowering from October to February in Glandorf, Germany. Flowers persistent.

*Postproduction longevity.*—Flowers last about ten days on the plant.

*Flower buds.*—Height: About 1.5 cm. Diameter: About 9 mm. Shape: Ovoid. Color: 145C.

*Flowers.*—Diameter: About 8 cm. Depth: About 3 cm.

*Petals.*—Size: Minute, obscured by reproductive organs; forming inconspicuous nectaries.

*Sepals.*—Quantity/arrangement per flower: Typically seven to nine in a single whorl. Length: About 3.5 cm. Width: About 3 cm. Shape: Broadly ovate. Apex: Broadly acute. Margin: Entire. Texture, upper and lower surfaces: Smooth, glabrous; satiny. Color: Developing sepals, upper and lower surfaces: 155D. Fully expanded sepals, upper and lower surfaces: 155D. Color becoming closer to 145B with development.

*Peduncles.*—Length: About 5 to 15 cm. Diameter: About 3 to 5 mm. Orientation: Upright. Strength: Very strong. Texture: Smooth, glabrous. Color: 145A. Pedicels: None.

*Reproductive organs.*—Stamens: Quantity per flower: About 80 to 100. Anther shape: Oblong. Anther length: About 2 mm. Anther color: 145C. Pollen amount: None observed. Pistils: Quantity per flower: About ten. Pistil length: About 1.2 cm. Stigma shape: Tuberculate. Stigma color: 155D to 145C. Style length: About 5 mm. Style color: 145C to 145D. Ovary color: 145C.

*Seed/fruit.*—Seed and fruit development have not been observed.

Disease/pest resistance: Plants of the new *Helleborus* have not been noted to be resistant to pathogens and pests common to *Helleborus*.

Temperature tolerance: Plants of the new *Helleborus* have been observed to tolerate temperatures from −15 to 36° C.

It is claimed:

1. A new and distinct cultivar of *Helleborus* plant named 'HGC Jericho', as illustrated and described.

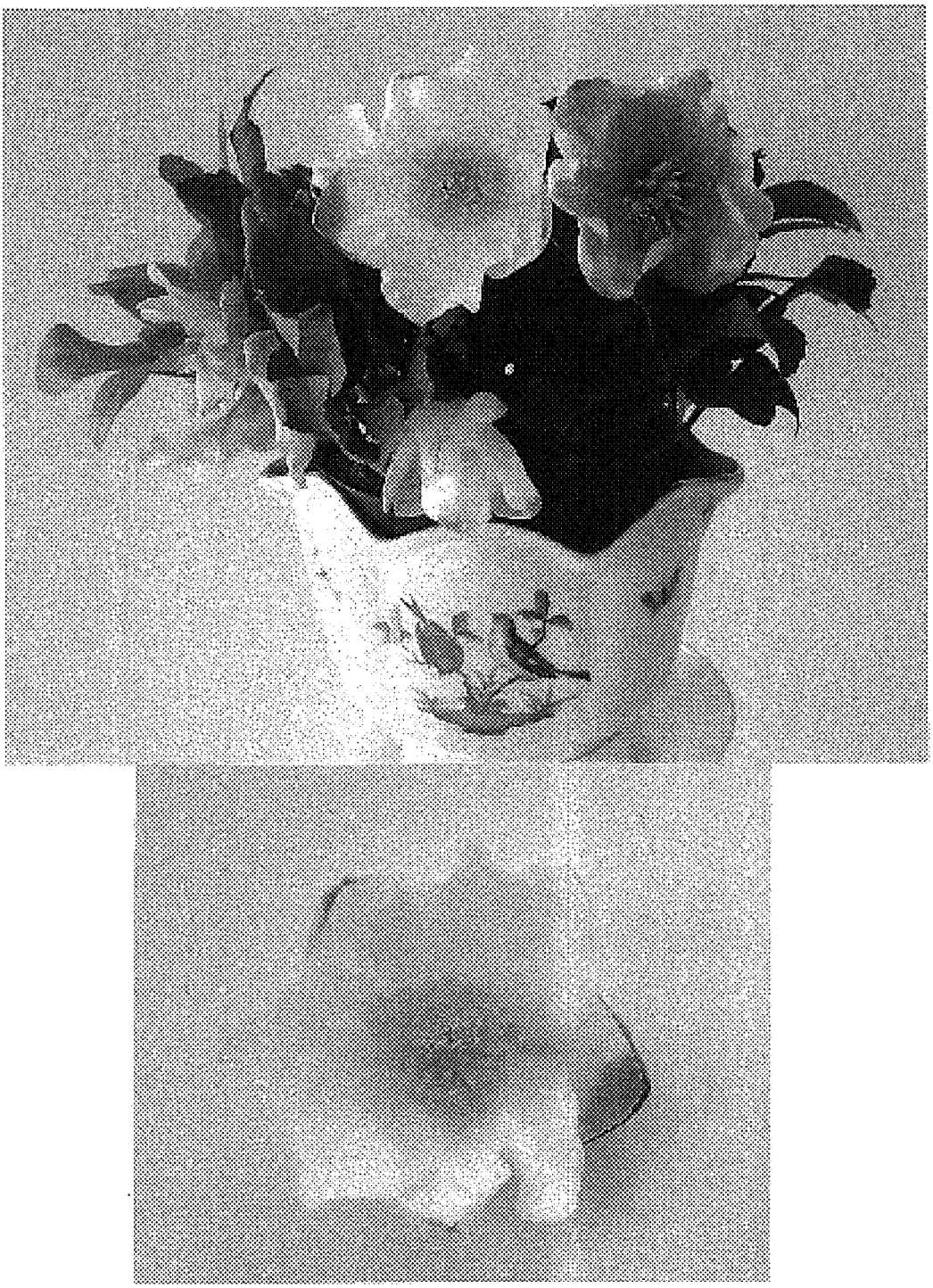

* * * * *